United States Patent [19]

Niimi et al.

[11] Patent Number: 5,462,864
[45] Date of Patent: Oct. 31, 1995

[54] MANUFACTURING METHOD OF HIGH PURITY MALTOSE AND ITS REDUCED PRODUCT

[75] Inventors: Masahiro Niimi, Ibaraki; Yukari Hariu, Shizuoka; Koichi Kataura, Shizuoka; Yoshibumi Ishii, Shizuoka; Kazuaki Kato, Saitama, all of Japan

[73] Assignee: Towa Chemical Industry Co., Ltd., Tokyo, Japan

[21] Appl. No.: 884,197

[22] Filed: May 18, 1992

Related U.S. Application Data

[62] Division of Ser. No. 425,714, Oct. 24, 1989, Pat. No. 5,141,859.

[30] Foreign Application Priority Data

Oct. 28, 1988 [JP] Japan .................... 63-270855

[51] Int. Cl.$^6$ .................. C12P 19/12; C12P 19/24; C12P 19/20; C12N 1/20
[52] U.S. Cl. ................. 435/100; 435/94; 435/95; 435/96; 435/99; 435/201; 435/202; 435/205; 435/210; 435/158; 435/252.3; 435/252.31; 536/124

[58] Field of Search ................ 435/94, 95, 96, 435/99, 100, 201, 202, 205, 210, 158, 252.3, 252.31; 536/124

[56] References Cited

U.S. PATENT DOCUMENTS

| | | | |
|---|---|---|---|
| 4,032,403 | 6/1944 | Sakai et al. | 435/95 |
| 4,675,293 | 6/1987 | Gibs | 435/95 |

OTHER PUBLICATIONS

Outtrup et al. "Properties and Application of a Thermostable . . . " Technical Bulletin A 05863 Apr. 1984.

*Primary Examiner*—Robert A. Wax
*Assistant Examiner*—Hyosuk Kim
*Attorney, Agent, or Firm*—Beveridge, DeGrandi, Weilacher & Young

[57] ABSTRACT

This invention allows high-purity maltose to be manufactured both simply and economically by sequentially going through the steps of liquefaction of starch, saccharification of the resulting liquefied substance by combining with general-purpose enzymes and further saccharification with an enzyme which hydrolyzes oligosaccharides of trisaccharide or more, and also allows the economical and favorable manufacturing of maltitol, the reduced product of the above maltose, by going through an additional reduction step.

22 Claims, 1 Drawing Sheet

FIG. 1

MANUFACTURING METHOD OF HIGH PURITY MALTOSE AND ITS REDUCED PRODUCT

This is a Division of application Ser. No. 07/425,714, filed Oct. 24, 1989, now U.S. Pat. No. 5,141,859.

BACKGROUND OF THE INVENTION

1) Field of the Invention

This invention relates to the manufacturing methods of high purity maltose and its reduced product.

2) Description of the Related Art

Maltose, 4-[α-D-glucopyranosyl]-D-glucose has been known as the main component of maltose starch syrup and used for a variety of foods because of its rich flavor.

On the other hand, maltitol, 4-[α-D-glucopyranosyl]-D-glutitol, the reduced product of the maltose, has found a variety of applications including foods, cosmetics, and medicines as it is less fermentable by the microorganisms and it contains sweet taste that is similar to sugar.

So far, it was harder to obtain high purity maltose or maltitol than to obtain high purity products of other saccharides. However, the attempts have been made to alleviate it by adopting specific saccharification method or by adopting the chromatographic separation method that has been used to improve the purity of other saccharides, to the manufacturing process of maltose or maltitol.

Among the many attempts to obtain high purity maltose or maltitol, the following are the typical cases.

(a) A method, as shown in Japanese TOKKYO-KOKAI-KOHO (18-month Publication of Unexamined Patent Application) SHOWA 57(1982)-134498 (hereinafter referred to as TOKKAISHO 57-134498), to obtain a high maltose liquid by acting β-amylase and isoamylase after liquefying starch to low DE (dextrose equivalent) with α-amylase.

(b) A method, as shown in Japanese TOKKAISHO 57-209000, TOKKAISHO 58-23799, TOKKAISHO 60-67000, TOKKAISHO 62-19210, to manufacture high purity maltose containing, for instance, not less than 93%, of maltose by performing a chromatographic separation for constituent of saccharified liquid that is chiefly composed of maltose with maltose purity of 75 through 85% (in this specification, "%" means "percentage by weight" per solid substance, unless otherwise stipulated) and contains less glucose with alkali metal strong acid cation exchange resin.

(c) A method, well-suited for manufacturing maltitol in the form of powder or crystal, as shown in Japanese TOKKYO-KOKOKU-KOHO (Publication of Examined Patent Application for Opposition) SHOWA 57(1982)-3356 (hereinafter referred to as TOKKOSHO 57-3356), TOKKOSHO 56-28153, TOKKOSHO 56-28154, to prepare maltose to which hydrogen has not yet been added, by acting, enzyme and the like (maltotriose resolutive activation/maltose resolutive activation is 2.5 or more) during saccharification.

(d) A method to obtain high purity maltitol—other than the method by reducing the maltose obtained through the above-mentioned methods, and undergoing several processings such as purification, separation, and crystallization—, as shown in Japanese TOKKAISHO 61-180797, by 1) liquefying the starch milk with a concentration of 25 through 457%, 2) saccharifying under the specified saccharification conditions, 3) obtaining saccharified liquid with the maltose purity of not less than 50 through 80%, 4) adding hydrogen to it, 5) performing a chromatographic separation, 6) obtaining sugar-alcohol liquid with the maltitol purity of 87 through 97.5%, 7) concentrating, and then 8) crystallizing it.

However, there are many problems to be solved with the conventional methods, and are not satisfactory as methods to manufacture high purity maltose or maltitol on a commercial basis.

For example, in the above-mentioned method (a), it is necessary to suppress, in liquefying the starch, the DE as low as possible. To put it concretely, it is necessary to suppress the DE not more than 2, preferably, 0.5 through 1.0 so as to obtain high purity maltose or maltitol.

To satisfy this DE value and values during the following processings, it is necessary to limit the raw material starch to expensive underground starch (potato starch, etc.) and suppress the liquefication concentration not more than 20% which is the lower value than that used for the conventional manufacturing process for high-maltose.

As a result, this method requires very large saccharification tank than that used for manufacturing high-maltose syrup or glucose syrup that are produced and distributed on a large scale. At the same time, it is necessary to concentrate a large amount of water, leading to a drawback of an increased concentration cost.

The above-mentioned method (b) is a method that allows to use inexpensive ground starch. The processing that is responsible for increasing the purity of maltose is a method to separate maltose from DP 3 or more (degree of polymerization), that is oligosaccharides of trisaccharide or more. In this method, however, it is extremely difficult to perform a separation because the molecular weight ratio of maltose and maltotriose is small and there is a small difference in the nature necessary for other separations, For this reason, a separation column with a great deal of capacity is required. A great deal of elution water is needed for separation. Thus, it requires a lot of concentration cost. These are the defects of this method. Furthermore, an entry of impurities such as glucose into maltose fraction, that takes place often because the separation is difficult, keeps us from obtaining high purity maltose.

The point of the above-mentioned. method (c) is that enzyme (maltotriose resolutive activation/maltose resolutive activation is 2.5 or more) and the like are acted during the saccharification. However, the defect is that it is difficult to obtain the enzyme because specific enzyme is used during saccharification. Another defect is that maltitol has to be produced from high purity maltose saccharification liquid obtained through saccharification by stopping the liquefaction at the level of around DE 1, because the increased glucose (because maltose is decomposed) keeps the yield of maltose at a low level.

In the above-mentioned method (d), the liquid used for separation is a mixture of sorbitol, maltitol, and sugar-alcohol of DP 3 or more. To take out a separation chiefly composed of maltitol, eight-column chromatographic separation unit has be operated in an extremely complicated manner.

Nonetheless, the separation status of each saccharin component is poor. Consequently, about 8% of maltotriitol can be seen in a fraction chiefly composed of maltitol.

The drawback of this method is that a contamination of sugar-alcohol of DP 3 or more checks the crystallization of maltitol, leading to a longer crystallization process and a lower yield of maltitol.

Because, moreover, the calcium type ion exchanger used for separation has a very strong adsorbing force against sorbitol, its elution is extremely slow as compared with maltitol or sugar-alcohol of DP 3 or more. As a result, chromatographic separation requires elution water five times the amount of raw material saccharification water. This means it is necessary to concentrate and remove a large amount of water, which is extremely inconvenient matter when viewed commercially.

Hence, a method for manufacturing high purity maltose and its reduced product which can solve the above-mentioned problems has been required.

SUMMARY OF THE INVENTION

The inventors of this invention, as a result of earnest researches, have found out more simple methods by decreasing, in case of maltose, the content of oligosaccharides (of DP 3 or more) such as maltotriose or maltotriose, or by decreasing, in case of maltitol, the content of oligosaccharide alcohols (of DP 3 or more) such as maltotriitol or maltotetraitol, in obtaining high purity powder maltose or maltitol through direct powdering and crystallization or in obtaining, at the final stage, high purity maltose or maltitol through chromatographic separation method or crystallization method when necessary.

Furthermore we succeeded in obtaining powder maltose and powder maltitol) combining general-purpose enzymes when even ground starch is used as raw material, 2) controlling the maltose purity 75 through 88%, 3) preparing it to saccharic composition with less oligosaccharides of trisaccharide or more, 4) and performing a crystallization or by 1) adding hydrogen to it, 2) and performing a direct powdering and crystallization. Moreover, we succeeded obtaining high purity maltose and maltitol by adopting chromatographic separation method or crystallization method when necessary.

The inventors have, as a result of earnest researches, developed a manufacturing method for an economically advantageous and simple high purity maltose as well as a manufacturing method for high purity maltitol by reducing high purity maltose, and invented this invention, by saccharifying it under specific conditions by using the maltogenic-α-amylase that is produced by preparing the plasmid to which a portion in which the maltogenic-α-amylase of gene of Bacillus stearothermophilus is coded, is built in, and setting this plasmid to Bacillus subtilis (which may be referred simply to as maltogenic-α-amylase, hereinafter).

One of the purposes of this invention is to provide a method to manufacture high purity maltose or high purity maltitol by partly using inexpensive ground starch and general-purpose enzyme through operations such as chromatographic separation when necessary in the realistic processings.

Another purpose of this invention is to provide a method to manufacture high purity maltose and its reduced product which has less oligosaccharides or less oligosaccharide alcohols and is easy to crystallize and powder, by using maltogenic-α-amylase and inexpensive ground starch in the simple and operatable processes.

This invention is a manufacturing method for high purity maltose and its reduced product and is composed of the following processings:

1. A method to manufacture high purity maltose using the following three processes.
   (1) No. 1 process of liquefying starch.
   (2) No. 2 process of saccharizing the obtained liquefied substance by using at least two enzymes selected from the group consisting of β-amylase, pullulanase and isoamylase.
   (3) No. 3 process of further saccharizing it, after the start of No. 2 process, by using an enzyme which hydrolyzes oligosaccharides of trisaccharide or more.

2. A method to manufacture high purity maltose as described in paragraph 1 above in which the No. 1 process is a process to be liquefied by heating the starch aqueous solution (with concentration 5 through 15%) to the starch paste.

3. A method to manufacture high purity maltose as described in paragraph 1 or 2 above in which the No. 3 process is a process to continue saccharification, for 10 through 48 hours from the beginning of the No. 2 process, by using maltogenic-α-amylase, 1 through 24 hours after starting the No. 2 process.

4. A method to manufacture high purity maltose as described in paragraph 1, 2 or 3 above, to obtain saccharic liquid containing 94.5% by weight or more of maltose per solid substance in the liquid by adjusting pH not more than 4.5, after the completion of No. 3 process, removing water insoluble components, hydrolyzing the dextrin in the liquid by using liquefying enzyme, and then purifying it.

5. A method to manufacture high purity maltose as described in paragraph 1 or 2 above in which the No. 3 process is a process to obtain saccharic liquid containing 94.5% by weight or more of maltose per solid substance in the liquid, by continuing saccharification, for 10 through 48 hours after the start of No. 2 process, for the saccharic liquid obtained after adjusting pH of the liquid to not more than 4.5 and removing the residue, 1 through 24 hours after the start of No. 2 process, by using maltogenic-α-amylase; thereafter, by hydrolyzing the dextrin in the liquid by using liquefying enzyme, filtrating and purifying.

6. A method to manufacture high purity maltose as described in paragraph 1 above, in which the No. 2 process is a process to saccharize the obtained liquefied substance to a maltose purity of 70% by weight or more in the solid part by using at least two enzymes selected from the group consisting of β-amylase, pullulanase and isoamylase, whereas, the No. 3 process is a process to saccharize the saccharification liquid obtained in the No. 2 process by using maltogenic-α-amylase until the value of the following formula (hereinafter may be referred simply as Formula-1) becomes not more than 8:

$$\frac{\text{(Weight of Solid Part of Oligosaccharides Being Trisaccharide or more)}}{\text{(Weight of Solid Part of Disaccharide)} + \text{(Weight of Solid Part of Oligosaccharides Being Trisaccharide or more)}} \times 100$$

7. A method to manufacture high purity maltitol using the following four processes.
   (1) No. 1 process of liquefying starch.
   (2) No. 2 process of saccharizing the obtained liquefied substance by using at least two enzymes selected from the group consisting of β-amylase, pullulanase and isoamylase.

(3) No. 3 process of further saccharizing it, after the start of No. 2 process, by using an enzyme which hydrolyzes oligosaccharides of trisaccharide or more.

(4) No. 4 process for reducing saccharic liquid after completion of the No. 3 process.

8. A method to manufacture high purity maltitol as described in paragraph 7 above in which the No. 1 process is a process to be liquefied by heating the starch aqueous solution (with concentration 5 through 15%) to the starch paste.

9. A method to manufacture high purity maltitol as described in paragraph 7 or 8 above in which the No. 3 process is a process to continue saccharification, for 10 through 48 hours from the beginning of the No. 2 process, by using maltogenic-α-amylase, 1 through 24 hours after starting the No. 2 process.

10. A method to manufacture high purity maltitol as described in paragraph 7, 8, or 9 above, to obtain saccharic liquid containing 94.5% by weight or more of maltose per solid substance in the liquid by adjusting pH not more than 4.5, after the completion of No. 3 process, removing water insoluble components, hydrolyzing the dextrin in the liquid by using liquefying enzyme, and then purifying it.

11. A method to manufacture high purity maltitol as described in paragraph 7 or 8 above in which the No. 3 process is a process to obtain saccharic liquid containing 94.5% by weight or more of maltose per solid substance in the liquid, by continuing saccharification, for 10 through 48 hours after the start of No. 2 process, for the saccharic liquid obtained after adjusting pH of the liquid to not more than 4.5 and removing the residue, 1 through 24 hours after the start of No. 2 process, by using maltogenic-α-amylase; thereafter, by hydrolyzing the dextrin in the liquid by using liquefying enzyme, filtrating and purifying.

12. A method to manufacture high purity maltitol as described in paragraph 7 above, in which the No. 2 process is a process to saccharize the obtained liquefied substance to a maltose purity of 70% by weight or more in the solid part by using at least two enzymes selected from the group consisting of β-amylase, pullulanase and isoamylase, whereas, the No. 3 process is a process to saccharize the saccharification liquid obtained in the No. 2 process by using glucoamylase until the value of the Formula-1 becomes not more than 8, and No. 4 process is a process to reduce the saccharification liquid after the No. 3 process and separate the obtained reduced product into the fractions of which main components are maltitol and other fractions by the chromatographic separation method.

13. A method to manufacture high purity maltitol as described in paragraph 12 above in which an adsorbent used for the chromatographic separation is a sodium type ion exchanger.

14. A method to manufacture high purity maltose using the following three processes.

(1) No. 1 process of liquefying starch to a ground starch aqueous solution with a concentration of 5 through 40% by weight by using liquefying enzyme, and deactivating the liquefying enzyme at not more than DE 15.

(2) No. 2 process of saccharizing the liquefied substance obtained by the above process by using at least two enzymes selected from the group consisting of β-amylase, pullulanase and isoamylase.

(3) No. 3 process of further saccharizing by using an enzyme for hydrolyzing oligosaccharides being trisaccharide or more after the start of the No. 2 process, having maltose purity of 75 through 90% by weight and limiting the value to not more than 8 when calculating it with Formula-1.

15. A method to manufacture high purity maltose as described in paragraph 14 above in which the concentration of ground starch is 10 through 30% by weight and liquefying enzyme is deactivated when DE after liquefaction is not more than 10, in the No. 1 process.

16. A method to manufacture high purity maltose as described in paragraph 14 above in which the No. 3 process is a process to saccharize by using maltogenic-α-amylase within 36 after the start of the No. 2 process. Further, 1 through 48 hours after the beginning of the No. 2 process, saccharize by using liquefying enzyme at the rate of 1 through 20 units per 1 g of substrate solid having maltose purity of 75 through 90 by weight and limiting the value to not more than 7 when calculating with Formula-1.

17. A method to manufacture high purity maltose as described in paragraph 14 or 15 above in which the No. 3 process is a process to saccharize by using liquefying enzyme at the rate of 1 through 20 units per 1 g of substrate solid 1 through 10 hours after the start of the No. 2 process. Further saccharize by using maltogenic-α-amylase at the rate of 1 through 20 units per 1 g of substrate solid having maltose purity of 75 through 88% by weight and limiting the value to not more than 8 when calculating with Formula-1.

18. A method to manufacture high purity maltose as described in paragraph 14 or 15 above in which the No. 3 process is a process to saccharize by using liquefying enzyme at the rate of 1 through 20 units per 1 g of substrate solid. Further saccharize by using glucoamylase at the rate of 0.1 through 10 units per 1 g of substrate solid having maltose purity of 75 through 88% by weight and limiting the value to not more than 8 when calculating with Formula-1.

19. A method to manufacture high purity maltitol using the following four processes.

(1) No. 1 process of liquefying starch to a ground starch aqueous solution with a concentration of 5 through 40% by weight by using liquefying enzyme, and deactivating the liquefying enzyme at not more than DE 15.

(2) No. 2 process of saccharizing the liquefied substance obtained by the above process by using at least two enzymes selected from the group consisting of β-amylase, pullulanase and isoamylase.

(3) No. 3 process of further saccharizing by using an enzyme for hydrolyzing oligosaccharides being trisaccharide or more after the start of the No. 2 process, having maltose purity of 75 through 90% by weight and limiting the value to not more than 8 when calculating it with Formula-1.

(4) No. 4 process of reducing the obtained saccharized substance.

20. A method to manufacture high purity maltitol as described in. paragraph 19 in which the concentration of ground starch is 10 through 30% by weight and liquefying enzyme is deactivated when DE after liquefaction is not more than 10, in the No. 1 process.

21. A method to manufacture high purity maltitol as described in paragraph 19 above in which the No. 3 process is a process to saccharize by using maltogenic-α-amylase within 36 hours after the start of the No. 2 process. Further saccharize by using liquefying enzyme at the rate of 1 through 20 units per 1 g of substrate solid having maltose purity of 75 through 90% by weight and limiting the value to not more than 7 when calculating with Formula-1.

22. A method to manufacture high purity maltitol as described in paragraph 19 or 20 above in which the No. 3 process is a process to saccharize by using liquefying enzyme at the rate of 1 through 20 units per 1 g of substrate solid 1 through 10 hours after the start of the No. 2 process. Further saccharize by using maltogenic-α-amylase at the rate of 1 through 20 units per 1 g of substrate solid having maltose purity of 75 through 88% by weight and limiting the value to not more than 8 when calculating with Formula-1.

23. A method to manufacture high purity maltitol as described in paragraph 19 or 20 above which the No. 3 process is a process to saccharize by using liquefying enzyme at the rate of 1 through 20 units per 1 g of substrate solid. Further saccharize by using glucoamylase at the rate of 0.1 through 10 units per 1 g of substrate solid having maltose purity of 75 through 88% by weight and limiting the value to not more than 8 when calculating with Formula-1.

DESCRIPTION OF THE PREFERRED EMBODIMENT

Both ground starch and underground starch can be used as a raw material in this invention and there is no need to worry about the composition of amylase and amylopectin in starch.

As concretely exemplifying starch usable for this invention, corn starch, potato starch, other kinds of starch from barley, sweet potato, tapioca, etc., can be mentioned here.

Also, the manufacturing method for high purity maltose and maltitol by this invention are as described in the above and one of these methods, for instance, can be explained as follows. Although it is unnecessary to limit conditions of liquefying starch, it is advantageous to liquefy with a jet cooker by using, for instance, heat resistant liquefying enzyme at the substrate concentration of 20 through 35%, and to deactivate liquefying enzyme at about DE 5 through 15 in order to improve economical efficiency by keeping high concentration and preventing the deterioration or liquefied substance by making its DE comparatively higher.

Furthermore, this liquefied solution is saccharized at 55° through 60° C. In this case, are used at least two enzymes selected from the group consisting of β-amylase, isoamylase and pullulanase. After that, further saccharize it by adding liquefying enzyme 1 through 10 hours after the start of the saccharification process making the maltose purity in the solid part 70% by weight or more.

By this second addition of the liquefying enzyme, oligosaccharides being not less than tetrasaccharide can be hydrolyzed, and as a result, improvement of both the maltose purity and solution filterability can be obtained. The saccharizing enzyme used at this time is enough to be on the market. Maltozyme® made by Nagase & company, Ltd., BBA 1500 by Finnish Sugar Co., Ltd and Biozyme® by Amano Pharmaceutical Co., Ltd. can be used as β-amylase, and Promozyme® made by Novo Industri A/S, Pullulanase Amano CKL, etc., can be used as pullulanase.

Next, though treating with either glucoamylase or maltagenic-α-amylase made by Novo Industri A/S, there is Gluczyme® made by Amano Pharmaceutical Co., Ltd., AMG200L and Maltogenase® by Novo Industri A/S as a usable enzyme at this time.

The purpose of this treatment by glucoamylase or maltogenic-α-amylase is to decrease the percentage of oligosaccharides being not less than trisaccharide to maltose. At this time, disaccharide can be partly hydrolyzed, but it is desirable to stop the hydrolysis of oligosaccharides being not less than trisaccharide at the point of making the maltose purity than 70% or more in the solid substance in the saccharic composition by progressing the hydrolysis and fulfilling the condition of the value obtained with Formula-1 being not more than 8.

The suitable saccharizing conditions are: a temperature of 50° through 60° C.; enzyme quantity of 1 through 20 units per 1 g of substrate solid (hereinafter may be referred to as DS); about pH 4.5 through 6.5, by which high purity maltose with maltose purity of 80 through 90% can be obtained.

The maltose purity of the maltose liquid obtained by the above can be purified by a method such as crystallization or chromatographic separation which are themselves well known. Then, make this treated liquid into a sugar-alcohol liquid of which a main component is maltitol by using a method such as batch type or continuous system, which are themselves well known, and by adding hydrogen under the existence of a catalyst such as a nickel-related metal or a noble metal-related metal. As for a condition of the hydrogen addition, although any condition can be acceptable unless the decomposition of maltose occurs, it is normally desirable to execute the addition at a temperature of 100° through 150° C. by making the concentration of the saccharified liquid 40 through 60% by weight, under hydrogen pressure of not less than 20 kg/cm$^2$, more preferably 50 through 200 kg/cm$^2$. Although it is unnecessary to drastically abate the non-reduced sugar after this hydrogen addition, it is desirable to make it not more than 1%, or preferably, not more than 0.5%.

After removing the catalyst according to necessity, and furthermore, if necessary, after executing activated carbon treatment, the obtained hydrogen additive liquid is used in the chromatographic separation process.

Chromatographic separation used in this invention can be executed by the batch type or the continuous system which are well known by using each kind of adsorbent.

If an ion exchanger used in this invention is a positive one, any ion exchange resin, ion exchange textile, zeolite, etc., may be used, but since a strong acidic cation exchange resin, in which the sulfonic group couples a bridge polymer of styrene-divinylbenzene substituted as a sodium type, is widely used as a product on the market, its use is more convenient. Also, it is in a good state of separation when eluting each adsorbed substance, compared with a calcium type, and furthermore, since the elution is not delayed, it is possible to make the capacity of separation column small. Therefore, since it is possible to execute chromatographic separation with a small amount of eluent, the concentration of fractions separated can be maintained high. By this, it is possible to decrease the quantity of water to concentrate in the following concentration process, and it a big economical advantage of this invention.

Also, since the main component of the sugar-alcohol composition substance composed by this invention is separated into fractions made up of maltitol and those of sorbitol, its separation efficiency is extremely high compared with that of conventional separation between fractions of which a main component is maltitol and those of which a main component is sugar-alcohol being not less than DP 3, and as a result, it also contributes to a decrease in capacity of the decrease and separation column in a quantity of the eluent.

The fractions of which the main component is maltitol obtained by this process have sufficient purity compared to maltitol sold on the market, and they can be liquid products when purified and concentrated by a well known method and also powdered or crystallized maltitol products, further concentrated and crystallized or powdered. As for methods of powdering, for instance, there can be the method of spray granulation, the kneader method, the method of fluid granulation, the method of block crushing, the method of crystallization centrifugal sugar, etc., or combinations of them. It is possible to make powders very easily because the maltitol liquid made by the method of this invention does include only a little oligosaccharide-alcohols with DP 3 or more considered to inhibit crystallization most and because of the high velocity of crystallization, even if any of the methods are used.

The process of manufacturing high purity maltose or high purity maltitol, which is industrially advantageous, from ground starch, which is economically advantageous, without going through complicated processes such as chromatographic separation, is also explained in the following.

First, heat the starch to a paste. It is desirable to do it under the condition of the concentration of the starch being 5 through 15% and a temperature of 10° through 160° C. in order to make the following process possible and obtain high purity maltose.

Then, execute the first step of saccharification of this pasted substance at a temperature of 55° through 60° C. and at the time, generate the saccharification effect by using at least two enzymes selected from the group consisting of β-amylase, pullulanase and isoamylase.

The time of saccharification until the second step of saccharification, that is, addition of maltogenic-α-amylase, from after the start of this saccharification process is supposed to be 1 through 24 hours, and it is desirable when the content of maltose in the substance dissolving in the water of the saccharized substance is 88% through 93% and more favorably becomes about 91 through 93%.

As for the saccharizing enzyme used for this first step of saccharification, β-amylase from soybeans has advantageous features for carrying out this invention.

Also, as pullulanase, Promozyme® made by Novo Industri A/S and Pullulanase Amano CKL by Amano Pharmaceutical Co., Ltd. are desirable because they are widely used and have advantageous features on the execution of this invention.

Next, saccharize by adding maltogenic-α-amylase. The suitable additive quantity is 3 through 20 u/g DS.

Then, after the completion of saccharification, adjust the pH to not more than 4.5 once. By this, it is possible not only to easily deactivate the enzyme but also to separate and remove the residue in the saccharized liquid.

After this, react it by adding liquefying enzyme. At the time, the desirable enzyme additive quantity is 0.1 through 30 u/g DS and the more favorable is 1 through 20 u/g DS. It is desirable that the reaction temperature and pH are 90° through 105° C. and about 5.0 through 6.0 respectively.

As for the standard of this reaction of enzyme, it is convenient to control with iodine reaction. It is most advantageous to add the enzyme when coloration no longer occurs for separating, removing and purifying the residue in the next process when coloration no longer occurs by iodine reaction.

After the above process, saccharized liquid with maltose content of not less than 94.5% in the solid part of the liquid by separating or removing the residue and purifying in the normal method.

Also, after adjusting the pH to not more than 4.5 and removing the residue after the No. 2 process of the invention described before, execute the second step of saccharification. The manufacturing of high purity maltose with not less than 94.5 purity an be done too by purifying after treating with liquefying enzyme under the same condition as that described before.

As a method of carrying out the removal of these insoluble matters in water or residue, it is possible to accept methods generally used in the starch saccharification industry such as the centrifugal separation method.

Also, as for liquefying enzyme used in this invention, α-amylase, etc., which are generally used in the starch industry are usable.

Although the high purity maltose obtained in the above process is such that it is possible to form a group of products of the maltose as it is or of powdered maltose, it is also possible to improve the maltose purity further by accepting crystallization and the chromatographic separation method according to necessity.

It is possible to make that which is obtained by this invention into high purity maltitol or crystallized maltitol by simply adding hydrogen. Furthermore, it is also possible to manufacture high purity maltitol and crystallized maltitol by adding hydrogen after improving the purity of the high purity maltose of this invention.

A method for manufacturing high purity maltose or high purity maltitol by this invention other than those described above is explained hereunder.

Both ground starch and underground starch can be used in this invention, and especially, ground starch, which has had many kinds of inconveniences so far in the case of manufacturing powdered maltose, powdered maltitol, high purity maltose or high purity maltitol, can be advantageously used, which is one of this invention's advantages. On executing this invention, there is especially no need to worry about the composition of amylose and amylopectin in this starch, and as showing concretely examples of usable starch, many kinds of underground starch as well as ground starch such as corn starch, wheat starch, and barley starch can be mentioned here.

If using ground starch as a raw material when liquefying these starches, it is desirable to saccharize by adjusting the substrate concentration at the time of liquefaction to 5 through 40%, or more favorably 10 through 30% and pH to 6.0 through 6.8, by using liquefying enzyme such as Termamil® (a registered trademark) made by Novo Industri A/S, for instance, and to deactivate the liquefying enzyme at not more than 15 dextrose equivalent, favorably not more than 13, or more favorably 3 through 10.

Next, saccharize by making β-amylase and pullulanase and/or isoamylase act on the liquefied substance. Its normal condition is: pH about 5.3 and temperature about 55° C. Further saccharize by adding liquefying enzyme at the rate of 1 through 20 per 1 g of substrate solid 1 through 10 hours after the start of saccharification process. This operation can dissolve oligosaccharides being tetrasaccharide or more and make a saccharic composition which further stimulates the effect manifestation of the No. 4 process by forming maltose and trisaccharide to improve filterability. Enzymes used in this case are β-amylase #1500 made by Nagase & company, Ltd. and Spezyme® (a registered trademark) BBA by Finnish Sugar Co., Ltd. as to β-amylase. As for pullulanase, there are Promozyme® by Novo Industri A/S, Pullulanase Amano CKL, etc., which are all widely used and sold on the market. Also, this process should be executed setting the standard of the period until the purity of maltose reaches equilibrium (normally 24 through 48 hours).

Then, add glucoamylase at the rate of 0.1 through 10 units per 1 g of substrate solid or maltogenic-α-amylase at the rate of 1 through 20 units after the completion of the No. 3 process to activate. AMG 200L made by Novo Industri A/S, Gluczyme® by Amano Pharmaceutical Co., Ltd., etc., are available as enzymes used in this case. Also, at this time, instead of glucoamylase, for instance, Maltogenase® (a registered trademark) made by Novo Industri A/S, which is a strong active maltogenic-α-amylase to hydrolyze oligosaccharides being not less than trisaccharide, can be advantageously used. This glucoamylase or maltogenic-α-amylase treatment process stops when the maltose purity is 75 through 88% by weight and within the range that the composition of the saccharized substance fulfills the condition of the valve of not more than 8 obtained with Formula-1. Although in this process disaccharide can also be hydrolyzed, since oligosaccharides being not less than trisaccharide is comparatively rapidly hydrolyzed, the value of Formula-1 drops, and then will rise if the reaction is stopped when the disaccharide being a solid substance shows a composition with the highest value. It is desirable as to increasing the yield of high purity maltose with a little oligosaccharides being not less than trisaccharide, that is, high purity maltose or high purity maltitol with highly crystallizable characteristics.

Make this treated liquid itself into a sugar-alcohol liquid of which a main component is maltitol by adding hydrogen under the existence of a catalyst such as a Nickel-related metal or a noble metal-related metal by a well known method such as the batch type or continuous system. If the dessolution of maltose does not occur, any condition in adding hydrogen can be accepted.

Since the obtained hydrogen added liquid has a considerably higher purity compared with maltitol currently on the market and the content of oligosaccharides being not less than trisaccharide in the constituent composition is little, direct crystallization and powdering by a well known method can be easily executed. After this, even if increasing the maltitol purity by the crystallization and chromatographic separation process, it is easier to separate maltitol by this method than any conventional method as it can extract the components based on mainly maltitol by any method to manufacture high purity maltitol.

As a method to obtain powdered maltitol, for instance, the method of spray granulation, the kneader method, the method of fluid granulation, the method of block crushing, the centrifugal sugar method, etc., and a combination of them can be used.

After this, if trying to heighten the maltitol purity according to necessity, a method to make an ion exchanger such as ion exchange resin, ion exchange textile, zeolite as an alkali metal type (especially a sodium type is advantageous) and execute chromatographic separation, and a method to crystallize and make centrifugal sugar after concentrating to the proper concentration can be used.

Another method for manufacturing high purity maltose or high purity maltitol by this invention other than those described above is explained hereunder.

When a material is ground starch, when saccharizing the starch, adjust the substrate concentration at the time of the saccharification to 5 through 40%, preferably 10 through 30% and the pH to 6.0 through 6.8. Saccharize by using liquefying enzyme with heat resistance such as Termamil® (a registered trademark) by Novo Industri A/S, and deactivate the liquefying enzyme at the dextrose equivalent of not more than 15, preferably 3 through 13.

Then, saccharize by making β-amylase, pullulanase and/ or isoamylase and maltogenic-α-amylase act on the liquefied substance at the same time as adding them or within 36 hours and its normally proper condition is: substrate concentration of 5 through 40% by weight; pH 5.3; temperature of 55° C.

Further saccharize by adding liquefying enzyme at the rate of 1 through 20 units per 1 g of substrate solid 1 through 48 hours after the start of this saccharification. However, by this operation, maltose and trisaccharide can form by hydrolyzing mainly oligosaccharides being not less than tetrasaccharide. After that, make them the saccharic composition with stimulates further effect manifestation in the process carried out, if necessary, to improve filterability. The suitable ratio of enzyme quantity used at the time of saccharification is: for instance, β-amylase 10 through 30 units and pullulanase 0.6 through 2.0 units when using maltogenic-α-amylase at the rate of 1 through 20 units. Also, this saccharification process can be executed, setting the standard of the period until the purity of maltose reaches equilibrium (normally 24 through 72 hours).

Although the liquefying enzyme used in this No. 3 process can be either that with heat resistance or that without heat resistance, liquefying enzyme without heat resistance is more effective in executing this invention.

By the above process, maltose purity of 75 through 90% by weight and within the value of not more than 7 can be saccharized when calculating the content of oligosaccharide in the saccharized substance with Formula-1.

The saccharized substance obtained by this process has comparatively higher maltose purity among products of which a main component is maltose currently on the market, and since the content of oligosaccharides being not less than trisaccharide, the viscosity is lower compared with similar products on the market. And since the rate of maltose crystallization is fast, it is easy to execute direct crystallization and powdering by a well known method. Furthermore, even if trying to heighten the purity by using the crystallization and chromatographic separation process, it can more advantageously manufacture high purity maltose than products manufactured by any conventional methods.

As a method to manufacture powdered high purity maltose, for instance, the centrifugal sugar method, the method of spray granulation, the fluid granulation method, the method of block crushing, and a combination of them can be used.

If heightening maltose purity according to necessity, a method to execute chromatographic separation by making an ion exchanger such as ion exchange resin, ion exchange textile, zeolite into an alkali metal type, and a method to crystallize and make centrifugal sugar after concentrating until proper concentration can be used.

Next, after heightening the maltose purity by any of the above methods according to necessity, or without doing so, hydrogen can be added under the existence of a reducing catalyst such as a nickel-related metal or a noble metal-related metal by simply using a well known method such as the batch type or continuous system to manufacture high purity maltitol.

High purity maltitol having little content of oligosaccharide, obtained by this process, has comparatively higher maltitol purity among products of which a main component is maltitol currently on the market, and since the content of oligosaccharide-alcohols being not less than trisaccharide-alcohol in the constituent composition is little, the viscosity is lower compared with similar products on the market. And since the rate of maltitol crystallization fast, it is easy to execute direct crystallization and powdering by a well known method.

After this, maltitol purity can be further heightened by well known methods such as the chromatographic separation method and the method of crystallization centrifugal sugar according to necessity.

EXAMPLE 1

(a) Step 1

After adjusting corn starch to a concentration of 32% and pH 6.3, adding 20 u/g substrate solid substance (abbreviated as DS) of heat resistant liquefying enzyme (Nagase & company, Ltd., Speedase® PN4), and liquefying at 105° C. with a jet cooker, the liquefaction reaction was halted at a DE of 12 by deactivating the enzyme.

(b) Step 2

After adjusting the liquefied liquid that was obtained to a temperature of 57° C. and pH 5.5, 1 ml/kg DS of β-amylase BBA1500 made by the Finnish Sugar Co. Ltd., and 1 u/g DS of pullulanase, Promozyme® TM200L made by the Novo Industri A/S, was added and the saccharification reaction was carried out. After 6 hours, 20 u/g DS of the above liquefying enzyme Speedase® PN4 was added and the saccharification reaction was allowed to proceed for another 30 hours. The results of analysis by high-pressure liquid chromatography of the saccharic components at that time are as indicated below.

| Monosaccharide | 1.7% |
| Disaccharide | 71.5% |
| Trisaccharide | 21.4% |
| Oligosaccharides of tetrasaccharide or more | 5.4% |

The above process in which liquefying enzyme was added during the reaction after 6 hours mainly produced maltose and trisaccharide by decomposing oligosaccharides of tetrasaccharide or more, and is an effective method for improving maltose purity and filterability.

(c) Step 3

Next, 1 u/g DS of glucoamylase (Gluczyme®, made by Amano Pharmaceutical Co. Ltd.,) was added and the reaction was allowed to proceed for an additional 10 hours. In this reaction, although disaccharide is hydrolyzed, oligosaccharides of trisaccharide or more are decomposed resulting in a decrease in the value calculated with Formula-1. When the reaction is allowed to proceed further, since this value reaches its maximum value, the reaction is brought to completion by heating after 10 hours, the point when the value is at its minimum.

The results of analysis by high-pressure liquid chromatography of the saccharic components at that time are as indicated below.

| Monosaccharide | 23.9% |
| Disaccharide | 70.6% |
| Trisaccharide | 1.5% |
| Oligosaccharides of tetrasaccharide or more | 4.0% |

(d) Step 4

The saccharified liquid obtained above was refined into a saccharic liquid having a concentration of 50% by decolorizing, demineralizing,and concentrating according to routine methods. 20 kg of this together with 200 g of Raney nickel catalyst were charged into an autoclave having an internal volume of 25 liters, maintained at a hydrogen pressure of 120 kg/cm$^2$ and stirred for 2 hours at 120° C. to carry out reduction. The results of analysis by high-pressure liquid chromatography after the liquid that was obtained was separated from the catalyst and passed through a column of granular activated carbon are as indicated below.

| Sorbitol | 24.6% |
| Maltitol | 70.2% |
| Oligosaccharide-alcohols of trisaccharide or more | 5.2% |

(e) Chromatographic Separation Process

Continuous separation by chromatographic separation of the above saccharic liquid having the main components of sorbitol and maltitol was performed by improving the method disclosed in Example 4 of U.S. Pat. No. 4,267,054 in which fructose and glucose are separated using a 4-column apparatus in order to adapt such method to the separation of the above saccharic liquid.

Figure 1:
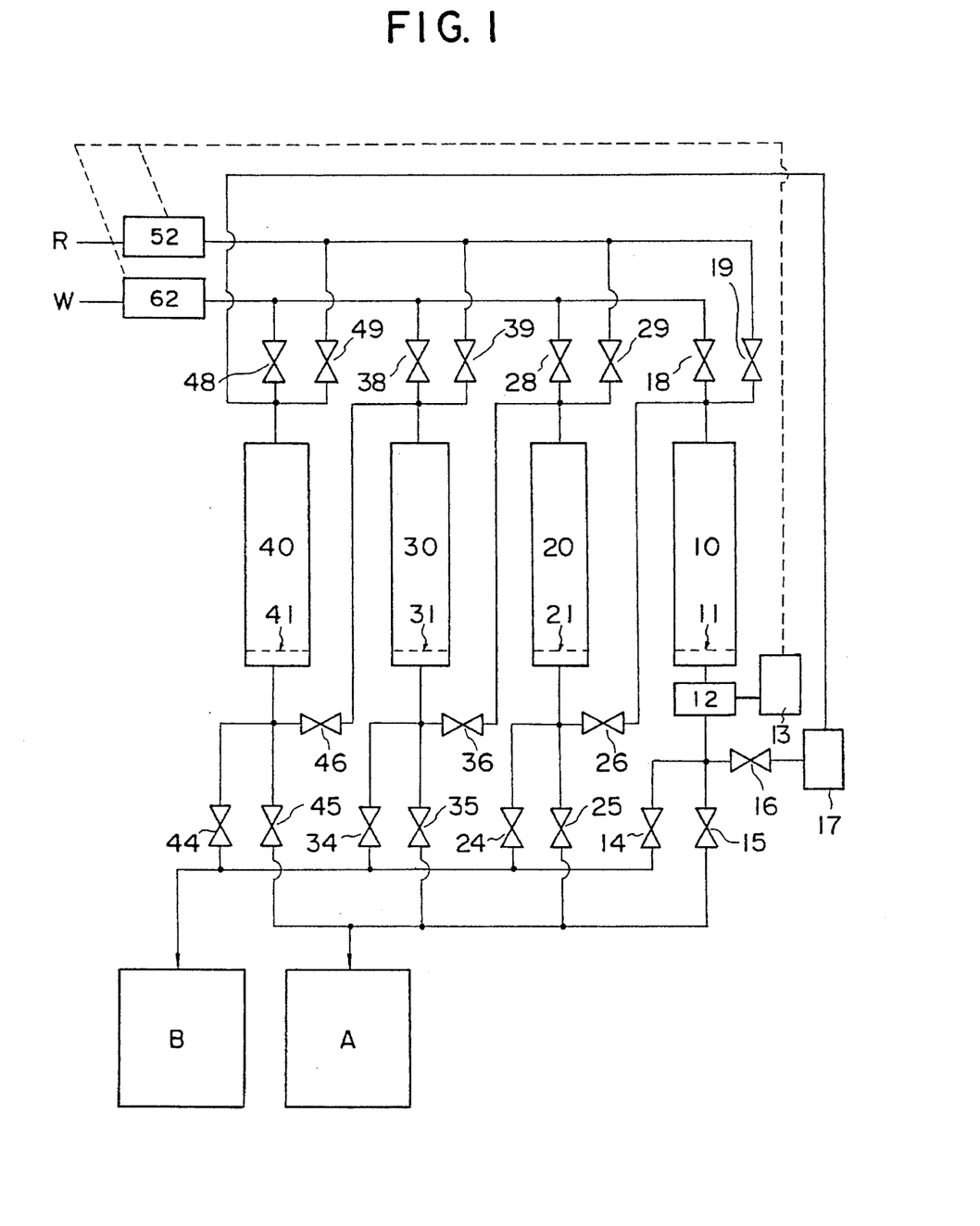
FIG. 1 is a rough drawing of the device to be used in the process of chromatographic separation.

FIG. 1 illustrates the composition of the columns and tubing. In this figure, 40, 30, 20 and 10 are separation columns, and into each of these columns is filled 75 liters of sodium-type, strongly acidic cation exchange resin (Diaion® FRK-01, Mitsubishi Kasei Corporation), respectively. The temperature inside the columns is maintained at 70° C. R is the entry for the raw material saccharic liquid for chromatographic separation obtained in Step 2, W is the entry for the elution water, A is the receptacle for the maltitol fraction and B is the receptacle for the sorbitol fraction. In addition, 12, 52 and 62 are preset flow meters, 13 and 17 are circulating pumps, 11, 21, 31 and 41 are filters and the other components are passage control valves.

The apparatus indicated in FIG. 1 were operated according to the procedure indicated in Table 1 below.

TABLE 1

| | | Flow Meter Preset Flow Rate (liter) | | |
|---|---|---|---|---|
| Step | No. of Open Valve | Flow Meter 12 | Flow Meter 52 | Flow Meter 62 |
| 1 | 48, 46, 36, 25 | — | — | 6.0 |
| 2 | 29, 25, 48, 44 | — | 11.0 | 7.2 |
| 3 | 46, 36, 26, 16 | 37.5 | — | — |
| 4 | 38, 36, 26, 15 | — | — | 6.0 |
| 5 | 19, 15, 38, 34 | — | 11.0 | 7.2 |
| 6 | 46, 36, 26, 16 | 37.25 | — | — |
| 7 | 28, 26, 16, 45 | — | — | 6.0 |
| 8 | 49, 45, 28, 24 | — | 11.0 | 7.2 |

TABLE 1-continued

| | | Flow Meter Preset Flow Rate (liter) | | |
|---|---|---|---|---|
| Step | No. of Open Valve | Flow Meter 12 | Flow Meter 52 | Flow Meter 62 |
| 9 | 46, 36, 26, 16 | 37.5 | — | — |
| 10 | 18, 16, 46, 35 | — | — | 6.0 |
| 11 | 39, 35, 18, 14 | — | 11.0 | 7.2 |
| 12 | 46, 36, 26, 16 | 37.5 | — | — |

In other words, when the valves specified according to the procedure in Table 1 are opened, the raw material saccharic liquid and water flow into the specified columns. At the same time, the maltitol and sorbitol fractions run out of the columns. When flow meters 52 and 62 reach the specified flow rates, the apparatus automatically shifts to the next step. In steps 3, 6, 9 and 12, all four columns are coupled together and the contents of all four columns are circulated by circulating pump 17. After flow meter 12 has reached the specified flow rate, the apparatus continues to the next step whereby step 12 goes back to step 1 and the process is repeated. Approximately 2 hours is required for 1 cycle.

The results of continuous operation for 24 hours are as indicated in Table 2 below. A saccharic liquid with a maltitol content of 90.2% was efficiently separated by chromatography at a concentration of 26.8%.

TABLE 2

| | Vol. liter/ day | Wgt. kg/ day | Solid Subst. kg/ day | Saccharic Comp. (%) | | |
|---|---|---|---|---|---|---|
| | | | | Sorbitol | Maltitol | Other |
| In | | | | | | |
| Raw Material Saccharic Liquid | 528 | 650 | 325 | 24.6 | 70.2 | 5.2 |
| Elution Water | 633 | 633 | — | — | — | — |
| Out | | | | | | |
| Sorbitol Fraction | 345 | 374 | 81 | 75.7 | 19.8 | 4.5 |
| Maltitol Fraction | 816 | 909 | 244 | 3.5 | 90.2 | 6.3 |

After the maltitol fraction obtained in this chromatographic separation step was purified and concentrated by routine methods, it was easily made into a powder by, for example, spray granulation, kneading, fluid granulation, block crushing or crystallization and centrifuging.

EXAMPLE 2

(a) Step 1

The starch concentration was adjusted to 30% in the same manner as in Example 1 and the liquefaction reaction was stopped at a DE of 7.

(b) Step 2

Next, the saccharification reaction was allowed to proceed by adding 25 u/g DS of β-amylase #1500 made by Nagase & company, Ltd. as β-amylase, 2 u/g DS of Pullulanase Amano CKL made by Amano Pharmaceutical Co., Ltd. as pullulanase, and then 10 u/g DS of liquefying enzyme Speedase® PN4 was added after 6 hours and the saccharification reaction was allowed to proceed another 48 hours. The results of analysis by high-pressure liquid chromatography of the saccharic components at that time are as indicated below.

| Monosaccharide | 0.7% |
|---|---|
| Disaccharide | 76.6% |
| Trisaccharide | 17.5% |
| Oligosaccharides of tetrasaccharide or more | 5.2% |

(c) Step 3

Next, 1 u/g DS of glucoamylase (Novo Industri A/S, AMG200L) was added and the reaction was allowed to proceed for an additional 8 hours.

The results of analysis by high-pressure liquid chromatography of the saccharic components at that time are as indicated below.

| Monosaccharide | 21.0% |
|---|---|
| Disaccharide | 73.5% |
| Trisaccharide | 3.2% |
| Oligosaccharides of tetrasaccharide or more | 2.3% |

(d) Step 4

The saccharification liquid obtained above was refined into a saccharic liquid having a concentration of 50% by decolorizing, demineralizing and concentrating according to routine methods. This was then reduced in the same manner as in Example 1 yielding the composition indicated below.

| Sorbitol | 21.7% |
|---|---|
| Maltitol | 73.0% |
| Oligosaccharide-alcohols of trisaccharide-alcohol or more | 5.3% |

(e) Chromatographic Separation Process The above sugar-alcohol liquid was separated by chromatography with the same method as that of Example 1. At that time, the preset flow rates of the flow meters were set changing the flow rate ratios of the fraction corresponding to the saccharic components as indicated in Table 3 below.

TABLE 3

| | | Flow Meter Pre-Set Flow Rate (liter) | | |
|---|---|---|---|---|
| Step | No. of Open Valve | Flow Meter 12 | Flow Meter 52 | Flow Meter 62 |
| 1 | 48, 46, 36, 25 | — | — | 6.3 |
| 2 | 29, 25, 48, 44 | — | 11.0 | 6.9 |
| 3 | 46, 36, 26, 16 | 37.5 | — | — |
| 4 | 38, 36, 26, 15 | — | — | 6.3 |
| 5 | 19, 15, 38, 34 | — | 11.0 | 6.9 |
| 6 | 46, 36, 26, 16 | 37.25 | — | — |
| 7 | 28, 26, 16, 45 | — | — | 6.3 |
| 8 | 49, 45, 28, 24 | — | 11.0 | 6.9 |
| 9 | 46, 36, 26, 16 | 37.5 | — | — |
| 10 | 18, 16, 46, 35 | — | — | 6.3 |
| 11 | 39, 35, 18, 14 | — | 11.0 | 6.9 |
| 12 | 46, 36, 26, 16 | 37.5 | — | — |

The results of chromatographic separation are indicated in Table 4.

TABLE 4

| | Vol. liter/ day | Wgt. kg/ day | Solid Subst. kg/ day | Saccharic Comp. (%) | | |
|---|---|---|---|---|---|---|
| | | | | Sorbitol | Maltitol | Other |
| In | | | | | | |
| Raw Material Saccharic Liquid | 528 | 650 | 325 | 21.7 | 73.0 | 5.3 |
| Elution Water | 633 | 633 | — | — | — | — |
| Out | | | | | | |
| Sorbitol Fraction | 302 | 331 | 78 | 73.6 | 22.2 | 4.2 |
| Maltitol Fraction | 859 | 952 | 247 | 3.0 | 91.3 | 5.7 |

The maltitol purity of this maltitol fraction was 91.3% and its concentration was 25.9%.

EXAMPLE 3

A sugar-alcohol was obtained via (a) Step 1 through (d) Step 4 of the saccharification process in the same manner as in Example 1.
(e) Chromatographic Separation Process
As oligosaccharide-alcohols of trisaccharide-alcohol or more move through the inside of a chromatographic separation column more rapidly than maltitol, a process was carried out which results in a low purity sorbitol liquid in which maltitol having a high purity was extracted separating into 3 fractions consisting of a sorbitol fraction, a maltitol fraction and an oligosaccharide-alcohols fraction having trisaccharide-alcohol or more, with the sorbitol fraction and oligosaccharide-alcohols fraction then collected in the same receptacle.

The process was carried out using the same apparatus as in Example 1 according to the procedure of Table 5.

Those results are as indicated in Table 6. A saccharic liquid was separated out which had a maltitol content of 95.1% and a concentration of 29.6%.

TABLE 5

| | | Flow Meter Pre-Set Flow Rate (liter) | | |
|---|---|---|---|---|
| Step | No. of Open Valve | Flow Meter 12 | Flow Meter 52 | Flow Meter 62 |
| 1 | 48, 46, 36, 25 | — | — | 3.0 |
| 2 | 29, 25, 48, 44 | — | 11.0 | 7.2 |
| 3 | 48, 46, 36, 26, 14 | — | — | 3.0 |
| 4 | 46, 36, 26, 16 | 37.5 | — | — |
| 5 | 38, 36, 26, 15 | — | — | 3.0 |
| 6 | 19, 15, 38, 34 | — | 11.0 | 7.2 |
| 7 | 38, 36, 26, 16, 44 | — | — | 3.0 |
| 8 | 46, 36, 26, 16 | 37.5 | — | — |
| 9 | 28, 26, 16, 45 | — | — | 3.0 |
| 10 | 49, 45, 28, 24 | — | 11.0 | 7.2 |
| 11 | 28, 26, 16, 46, 34 | — | — | 3.0 |
| 12 | 46, 36, 26, 16 | 37.5 | — | — |
| 13 | 18, 16, 46, 35 | — | — | 3.0 |
| 14 | 39, 35, 18, 14 | — | 11.0 | 7.2 |
| 15 | 18, 16, 46, 36, 24 | — | — | 3.0 |
| 16 | 46, 36, 26, 16 | 37.5 | — | — |

TABLE 6

| | Vol. liter/ day | Wgt. kg/ day | Solid Subst. kg/ day | Saccharic Comp. (%) | | |
|---|---|---|---|---|---|---|
| | | | | Sorbitol | Maltitol | Other |
| In | | | | | | |
| Raw Material Saccharic Liquid | 528 | 650 | 325 | 24.6 | 70.2 | 5.2 |
| Elution Water | 633 | 633 | — | — | — | — |
| Out | | | | | | |
| Sorbitol Fraction | 489 | 528 | 100 | 72.9 | 14.1 | 13.0 |
| Maltitol Fraction | 672 | 761 | 225 | 3.1 | 95.1 | 1.8 |

EXAMPLE 4

(a) Step 1
Corn starch was adjusted to a concentration of 32% and pH 6.3 and then liquefied at 105° C. with a jet cooker after adding 20 u/g DS of heat resistant liquefying enzyme (Nagase & company, Ltd, Speedase HS). Liquefaction was halted at a DE of 12 by deactivating the liquefying enzyme.
(b) Step 2
Next, the liquefied liquid was adjusted to pH 5.5, and the saccharification reaction was allowed to proceed by adding 1 ml/kg DS of Spezyme BBA1500 made by the Finnish Sugar Co. Ltd., and 1 u/g DS of pullulanase, Promozyme® TM200L made by the Novo Industri A/S, at 57° C. The saccharification reaction was allowed to proceed for a total of 36 hours after adding 20 u/g DS of liquefying enzyme Speedase® PN4 in the sixth hour of the reaction. The results of analysis by high-pressure liquid chromatography of the saccharic components 36 hours after beginning the saccharification reaction are as indicated below.

| Monosaccharide | 1.0% |
|---|---|
| Disaccharide | 72.8% |
| Trisaccharide | 21.2% |
| Oligosaccharides of tetrasaccharide or more | 5.0% |

(c) Step 3
Continuing, high-purity maltose (1) was obtained by continuing the reaction for an additional 36 hours adding 10 u/g DS of maltogenic-α-amylase (Novo Industri A/S, Maltogenase®). The results of analysis by high-pressure liquid chromatography of the saccharic composition following completion of the reaction are as indicated below.

| Monosaccharide | 9.8% |
|---|---|
| Disaccharide | 84.1% |
| Trisaccharide | 1.9% |
| Oligosaccharides of tetrasaccharide or more | 4.2% |

EXAMPLE 5

Other than changing the concentration of the corn starch to 25% and the liquefaction DE to 6, the liquid having the saccharic composition indicated below was obtained using the same procedures as those of Step 1 and Step 2 of Example 1.

| | |
|---|---|
| Monosaccharide | 0.7% |
| Disaccharide | 80.5% |
| Trisaccharide | 14.7% |
| Oligosaccharides of tetrasaccharide or more | 4.1% |

In addition, other than changing the addition amount of Maltogenase® to 5 u/g DS, high-purity maltose (2) was obtained having the saccharic composition indicated below using the same procedure as that of Step 3 of Example 4.

| | |
|---|---|
| Monosaccharide | 5.5% |
| Disaccharide | 88.9% |
| Trisaccharide | 1.6% |
| Oligosaccharides of tetrasaccharide or more | 4.0% |

EXAMPLE 6

The high-purity maltose (1) obtained in Example 4 was concentrated into a saccharic liquid having a concentration of 50% by decolorizing, demineralizing and concentrating according to routine methods. Hydrogenation was performed by charging 20 kg of this saccharic liquid together with 200 g of Raney nickel catalyst into an autoclave having an internal volume of 25 liters, maintaining the hydrogen pressure at 120 kg/cm$^2$, and stirring for 2 hours at 120° C. The reaction liquid that was obtained was separated from the catalyst and passed through a column of granular activated carbon. The results of analysis by high-pressure liquid chromatography are as indicated below.

| | |
|---|---|
| Sorbitol | 10.3% |
| Maltitol | 83.8% |
| Oligosaccharide-alcohols of trisaccharide-alcohol | 5.9% |

EXAMPLE 7

The high-purity maltose (2) obtained in Example 5 was concentrated to a saccharic liquid having a concentration of 50% by decolorizing, demineralizing and concentrating according to routine methods. Hydrogenation was performed in the same manner as in Example 6. The results of analysis by high-pressure liquid chromatography after the following purification procedure are as indicated below.

| | |
|---|---|
| Sorbitol | 5.7% |
| Maltitol | 88.5% |
| Oligosaccharide-alcohols of trisaccharide-alcohol | 5.8% |

EXAMPLE 8

(a) Step 1

Corn starch was adjusted to a concentration of 11% and formed into a paste by heating at 120° C. for 20 minutes.

(b) Step 2

The paste liquid was adjusted to a pH of 5.5 and the saccharification reaction was carried out at a temperature of 57° C. for 6 hours adding 1 ml/kg DS of spezyme BBA1500 made by the Finnish Sugar Co. Ltd. and 1 u/g DS of Promozyme® TM200L made by the Novo Industri A/S.

(c) Step 3

After 6 hours from the starting of saccharification, 5 u/g DS of Maltogenase® made by the Novo Industri A/S were added and the saccharification reaction was continued for an additional 24 hours.

The results of analysis by high-pressure liquid chromatography of the saccharic composition following the completion of saccharification of Step 3 are as indicated below.

| | |
|---|---|
| Monosaccharide | 1.7% |
| Disaccharide | 95.8% |
| Trisaccharide | 0.5% |
| Oligosaccharides of tetrasaccharide or more | 2.0% |

Following the saccharification of Step 3, the enzyme was deactivated adjusting to the pH to 3.5. Those components insoluble in water were removed by centrifugal sedimentation. 20 u/g DS of α-amylase were added and the reaction was allowed to proceed until the solution no longer demonstrated an iodine reaction at a temperature of 100° C. The solution was filtered and purified to obtain high-purity maltose.

The results of analysis of this substance by high-pressure liquid chromatography are as indicated below.

| | |
|---|---|
| Monosaccharide | 1.7% |
| Disaccharide | 95.5% |
| Trisaccharide | 0.7% |
| Oligosaccharides of tetrasaccharide or more | 2.1% |

EXAMPLE 9

(a) Step 1

Other than changing the temperature in Example 8 to 150° C., the corn starch was formed into a paste by heating in the same manner as in Step 1 of Example 8.

(b) Step 2

Other than changing the paste liquid from the β-amylase of Example 8 to β-amylase #1500 made by Nagase & company, Ltd., the saccharification reaction was performed for 24 hours in the same manner as in Step 2 of Example 8.

The results of analysis by high-pressure liquid chromatography of the saccharic composition in the 24th hour following beginning of saccharification are as indicated below.

| | |
|---|---|
| Monosaccharide | Not Detected |
| Disaccharide | 92.5% |
| Trisaccharide | 5.0% |

| | |
|---|---|
| Oligosaccharides of tetrasaccharide or more | 2.5% |

(c) Step 3

The pH was adjusted to 3.0 the 24th hour following beginning of saccharification, the residue was removed by centrifugal separation, 10 u/g DS of Maltogenase® made by the Novo Industri A/S were added at a pH of 5.3, and the saccharification reaction was then allowed to continue for an additional 24 hours.

1 u/g DS of α-amylase was added in the 24th hour following the beginning of Step 3 and was allowed to react at 100° C. until the solution no longer demonstrated an iodine reaction. Those components insoluble in water were filtered and the solution was purified to obtain high-purity maltose.

The results of analysis by high-pressure liquid chromatography of this substance are as indicated below.

| | |
|---|---|
| Monosaccharide | 1.5% |
| Disaccharide | 95.1% |
| Trisaccharide | 0.4% |
| Oligosaccharides of tetrasaccharide or more | 3.0% |

EXAMPLE 10

(a) Step 1

Corn starch was adjusted to a concentration of 18% and pH 6.3 and liquefied at a temperature of 105° C. with routine methods adding 5 u/g DS of heat resistant liquefying enzyme (Nagase & company, Ltd., Speedase HS). The liquefaction reaction was halted at a DE of 1.9 by heating.

(b) Step 2

Next, after adjusting to a temperature of 57° C. and pH of 5.5, the saccharification was allowed to proceed by adding 30 u/g DS of β-amylase #1500 made by Nagase & company, Ltd. and 2 u/g DS of Promozyme® TM200L made by Novo Industri A/S.

Further, 20 u/g DS of Speedase PN4 was added in the 6th hour following the beginning of Step 2 and the saccharification reaction was allowed to proceed for an additional 39 hours. The results of measurement by high-pressure liquid chromatography of the saccharic components following completion of Step 2 are as indicated below.

| | |
|---|---|
| Monosaccharide | 1.3% |
| Disaccharide | 86.0% |
| Trisaccharide | 10.6% |
| Oligosaccharides of tetrasaccharide or more | 2.1% |

After the above six hours, the step in which liquefying enzyme is added during saccharification reduces the amount of oligosaccharides of trisaccharide or more making it effective in improving filterability.

(c) Step 3

Next, the reaction was allowed to proceed for an additional 9 hours following the addition of 1 u/g DS of glucoamylase (Amano Pharmaceutical Co., Ltd., Gluczyme). In this reaction, although disaccharide is decomposed, oligosaccharides of trisaccharide or more are comparatively rapidly hydrolyzed resulting in a decrease in the value calculated with Formula-1. When the reaction is allowed to proceed further, since this value will eventually increase, the reaction was halted by heating after approximately 7 hours, the point where this value is at its minimum, to obtain the high-purity maltose of this invention.

The results of analysis by high-pressure liquid chromatography of the saccharic components at this time are as indicated below.

| | |
|---|---|
| Monosaccharide | 9.3% |
| Disaccharide | 84.8% |
| Trisaccharide | 3.5% |
| Oligosaccharides of tetrasaccharide or more | 2.4% |

Value of Formula-1 = 6.5

(d) Step 4

The high-purity maltose obtained above was purified into a saccharic liquid having a concentration of 50% by decolorizing, demineralizing and concentrating according to routine methods. Reduction was performed by charging 20 kg of this saccharic liquid together with 200 g of Raney nickel catalyst into an autoclave having an internal volume of 25 liters, maintaining at 120° C., at a hydrogen pressure of 120 kg/cm$^2$ and stirring for 2 hours. After separating the resulting liquid from the catalyst, the liquid was passed through a column of granular activated carbon to obtain the high-purity maltitol. The results of analysis of this high-purity maltitol by high-pressure liquid chromatography are as indicated below.

| | |
|---|---|
| Sorbitol | 10.1% |
| Maltitol | 84.2% |
| Oligosaccharide-alcohols of trisaccharide-alchohol or more | 5.7% |

EXAMPLE 11

(a) Step 1

Corn starch was adjusted to a concentration of 18% and pH of 6.3 and liquefied at 105° C. with routine methods adding 5 u/g DS of heat resistant liquefying enzyme (Nagase & company, Ltd., Speedase HS). The liquefaction reaction was halted at a DE of 1.9 by heating.

(b) Step 2

Next, after adjusting to a temperature of 57° C. and a pH of 5.5, the saccharification reaction was allowed to proceed by adding 30 u/g DS of β-amylase #1500 made by Nagase & company, Ltd. and 2 u/g DS of Promozyme® TM200L made by Novo Industri A/S.

Further, the saccharification reaction was allowed to proceed for an additional 39 hours adding 20 u/g DS of above Speedase PN4 in the 6th hour following the beginning of Step 2. The results of measurement by high-pressure liquid chromatography of the saccharic composition following completion of Step 2 are as indicated below.

| | |
|---|---|
| Monosaccharide | 1.3% |
| Disaccharide | 86.0% |
| Trisaccharide | 10.6% |
| Oligosaccharides of tetrasaccharide | 2.1% |

-continued

| | |
|---|---|
| or more | |

The step in which liquefying enzyme is added during saccharification after the above 6 hours reduces the amount of oligosaccharides of trisaccharide or more making it an effective method in improving filterability.

(c) Step 3

Next, the reaction was allowed to proceed an additional 9 hours adding 1 u/g DS of glucoamylase (Amano Pharmaceutical Co., Ltd., Gluczyme). In this reaction, although disaccharides are hydrolyzed, since oligosaccharides of trisaccharide or more are hydrolyzed comparatively rapidly, the value calculated in Formula-1 is reduced. When the reaction is allowed to proceed further, since this value eventually increases, the reaction was halted by heating after approximately 7 hours, the point at which this value is at a minimum, to obtain the high-purity maltose.

The results of analysis by high-pressure liquid chromatography of the saccharic components at this time are as indicated below.

| | |
|---|---|
| Monosaccharide | 9.3% |
| Disaccharide | 84.8% |
| Trisaccharide | 3.5% |
| Oligosaccharides of tetrasaccharide or more | 2.4% |

Value of Formula-1 = 6.5

(d) Step 4

The high-purity maltose obtained above was purified into a saccharic liquid having a concentration of 50% by decolorizing, demineralizing and concentrating according to routine methods. Reduction was performed by charging 20 kg of this saccharic liquid together with 200 g of Raney nickel catalyst into an autoclave having an internal volume of 25 liters, maintaining at 120° C., at a hydrogen pressure of 120 kg/cm$^2$ and stirring for 2 hours. After separating the resulting liquid from the catalyst, the liquid was passed through a column of granular activated carbon. The results of analysis by high-pressure liquid chromatography of this saccharic liquid are as indicated below.

| | |
|---|---|
| Sorbitol | 10.1% |
| Maltitol | 84.2% |
| Oligosaccharide-alcohols of trisaccharide-alcohol or more | 5.7% |

EXAMPLE 12

Steps 1 and 2 were carried out in the same manner as in Example 11 and the reaction was allowed to progress further adding adding 5 u/g DS of Maltogenase® made by Novo Industri A/S (Maltogenic Amylase Novo Unit) to the resulting saccharified substance. The reaction was halted in the 24th hour of the reaction by heating to obtain the high-purity maltose. The results of analysis by high-pressure liquid chromatography of the saccharic components of this high-purity maltose are as indicated below.

| | |
|---|---|
| Monosaccharide | 6.3% |

-continued

| | |
|---|---|
| Disaccharide | 89.1% |
| Trisaccharide | 0.9% |
| Oligosaccharides of tetrasaccharide or more | 3.7% |

Value of Formula-1 = 4.9

EXAMPLE 13

(a) Step 1

Corn starch was adjusted to a concentration of 30% and pH of 6.2 and liquefied at 105° C. with routine methods adding 20 u/g DS of heat resistant liquefying enzyme (Nagase & company, Ltd., Speedase HS). The liquefaction reaction was halted at a DE of 6.5 by heating.

(b) Step 2

Next, after adjusting to a temperature of 55° C. and a pH of 5.3, the saccharification reaction was allowed to proceed by adding 10 u/g DS of β-amylase #1500 made by Nagase & company, Ltd., and 0.67 u/g DS of Promozyme® TM200L made by Novo Industri A/S.

6.5u/g DS of Maltogenase® made by Novo Industri A/S were then added in the 6th hour following beginning of Step 2.

(c) Step 3

Further, the saccharification reaction was allowed to continue for an additional 66 hours adding 20 u/g DS of the above Speedase PN4 in the 6th hour following the beginning of Step 2 to obtain the high-purity maltose.

The results of measurement by high-pressure liquid chromatography of the saccharic composition following completion of Step 3 are as indicated below.

| | |
|---|---|
| Monosaccharide | 7.0% |
| Disaccharide | 88.2% |
| Trisaccharide | 1.0% |
| Oligosaccharides of tetrasaccharide or more | 3.8% |

EXAMPLE 14

The saccharified substance obtained in Example 13 was purified into a saccharic liquid having a concentration of 50% by decolorizing, demineralizing and concentrating according to routine methods. Reduction was performed by charging 20 kg of this saccharic liquid together with 200 g of Raney nickel catalyst into an autoclave having an internal volume of 25 liters, maintaining at 120° C., at a hydrogen pressure of 120–150 kg/cm$^2$ and stirring for 2 hours to obtain a high-purity maltitol liquid. After separating the resulting liquid from the catalyst, the liquid was passed through a column of granular activated carbon. The results of analysis by high-pressure liquid chromatography of this maltitol liquid are as indicated below.

| | |
|---|---|
| Sorbitol | 7.4% |
| Maltitol | 88.1% |
| Oligosaccharide-alcohols of trisaccharide-alcohol or more | 4.5% |

After purifying the resulting high-purity maltitol, concentrating to a concentration of 75 and cooling to 10° C., a mascuite was prepared by the addition and mixing in of 3% by weight seed crystal over the course of 15 hours while stirring. Spray crystallization was then performed with a blow dryer at a blast temperature of 80° C. to obtain the crystalline high-purity maltitol.

Comparative Example 1

For the sake of comparison, commercially available maltose liquid (saccharic composition: monosaccharide 1.4%, disaccharide 90.0%, trisaccharide 7.0%, oligosaccharides of tetrasaccharide or more 1.6%) was reduced to obtain the reduced product having the composition indicated below.

| | |
|---|---|
| Sorbitol | 1.5% |
| Maltitol | 89.6% |
| Oligosaccharide-alcohols of trisaccharide-alcohol or more | 8.9% |

Although he procedure for preparing the mascuite was performed after purification, concentration and cooling in the same manner as in Example 14, a mascuite was unable to be obtained which could be blow dried after 15 hours.

What we claim is:

1. A method to manufacture high purity maltitol using the following four processes:

(a) process of liquefying starch to produce a liquefied substance, (b) process of saccharifying the obtained liquefied substance by using at least two enzymes selected from the group consisting of β-amylase, pullulanase and isoamylase, (c) process of further saccharifying the obtained liquefied substance, after the start of the (b) process, by using glucoamylase or maltogenic-α-amylase which is produced by inserting the portion of the gene of *Bacillus stearothermophilus* coding for maltogenic-α-amylase into *Bacillus subtilis*, and (d) process for reducing saccharic liquid after completion of the (c) process utilizing a nickel or noble metal catalyst.

2. The method to manufacture high purity maltitol as described in claim 1, wherein the (a) process is a process to liquefy starch by heating the starch aqueous solution with concentration 5 through 15% to the liquefied starch.

3. The method to manufacture high purity maltitol as described in claim 1, wherein saccharic liquid containing 94.5% by weight or more of maltose per solid substance in the liquid is obtained by adjusting pH not more than 4.5, after the completion of the (c) process, removing water insoluble components, hydrolyzing the dextrin in the liquid by using liquefying enzyme, and then purifying the hydrolyzate derived therefrom.

4. The method to manufacture high purity maltitol as described in claim 1, wherein the (b) process is a process to saccharify the obtained liquefied substance to a maltose purity of 70% by weight or more in the solid part by using at least two enzymes selected from the group consisting of β-amylase, pullulanase and isoamylase, whereas, the (c) process is a process to saccharify the saccharification liquid obtained in the (b) process by using glucoamylase until the value of the following formula becomes not more than 8:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

and the (d) process is a process to reduce the saccharification liquid after the (c) process by utilizing a nickel or noble metal catalyst and separate the obtained reduced product into the fractions of which main components are maltitol and other fractions by the chromatographic separation method.

5. A method to manufacture high purity maltitol using the following four processes:

(a) process of liquefying starch to a ground starch aqueous solution with a concentration of 5 through 40% by weight by using liquefying enzyme, and deactivating the liquefying enzyme at not more than DE 15, (b) process of saccharifying the liquefied substance obtained by the above process by using at least two enzymes selected from the group consisting of β-amylase, pullulanase and isoamylase, (c) process of further saccharifying the obtained liquefied substance by using glucoamylase or maltogenic-α-amylase, which is produced by inserting the portion of the gene of *Bacillus stearothermophilus* coding for maltogenic-α-amylase into *Bacillus subtilis*, after the start of the (b) process, having maltose purity of 75 through 90% by weight and limiting the value to not more than 8 when calculating it with the following formula:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

and (d) process of reducing the obtained saccharified substance by utilizing a nickel or noble metal catalyst.

6. The method to manufacture high purity maltitol as described in claim 5, wherein the concentration of ground starch is 10 through 30% by weight and liquefying enzyme is deactivated when DE after liquefaction is not more than 10, in the (a) process.

7. The method to manufacture high purity maltitol as described in claim 5, wherein the (c) process is a process to saccharify by using liquefying enzyme at the rate of 1 through 20 units per 1 g of substrate solid, further saccharify by using glucoamylase at the rate of 0.1 through 10 units per 1 g of substrate solid within a range such that maltose purity is 75 through 88% by weight and the value which is calculated with the following formula is not more than 8:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

8. The method to manufacture high purity maltitol as described in claim 2, wherein saccharic liquid containing 94.5% by weight or more of maltose per solid substance in the liquid is obtained by adjusting pH not more than 4.5, after the completion of (c) process, removing water insoluble components, hydrolyzing the dextrin in the liquid by using liquefying enzyme, and then purifying the hydrolysate derived thereof.

9. The method to manufacture high purity maltitol as described in claim 6, wherein the (c) process is a process to saccharify by using liquefying enzyme at the rate of 1 through 20 units per 1 g of substrate solid, further saccharify by using glucoamylase at the rate of 0.1 through 10 units per 1 g of substrate solid within a range such that maltose purity is 75 through 88% by weight and the value which is calculated with the following formula is not more than 8:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

10. The method to manufacture high purity maltitol as described in claim 1, wherein the (c) process is a process to continue saccharification, for 10 through 48 hours from the beginning of the (b) process, by using maltogenic-α-amylase which is produced by inserting the portion of the gene of *Bacillus stearothermophilus* coding for maltogenic-α-amylase into a plasmid and incorporating into *Bacillus subtilis*, 1 through 24 hours after starting the (b) process.

11. The method to manufacture high purity maltitol as described in claim 10, wherein saccharic liquid containing 94.5% by weight or more of maltose per solid substance in the liquid is obtained by adjusting pH not more than 4.5, after the completing of the (c) process, removing water insoluble components, hydrolyzing the dextrin in the liquid by using liquefying enzyme, and then purifying the hydrolyzate derived therefrom.

12. The method to manufacture high purity maltitol as described in claim 1, wherein the (c) process is a process to obtain saccharic liquid containing 94.5% by weight or more of maltose per solid substance in the liquid, by continuing saccharification, for 10 through 48 hours after the start of the (b) process, for the saccharic liquid from the (b) process 1 through 24 hours after the start of the (b) process obtained after adjusting pH of the liquid to not more than 4.5 and removing the residue, by using maltogenic-α-amylase which is produced by inserting the portion of the gene of *Bacillus stearothermophilus* coding for maltogenic-α-amylase into a plasmid and incorporating into *Bacillus subtilis*; thereafter, by hydrolyzing the dextrin in the liquid by using liquefying enzyme, filtrating and purifying the hydrolysate derived thereof.

13. The method to manufacture high purity maltitol as described in claim 5, wherein the (c) process is a process to saccharify by using maltogenic-α-amylase within 36 hours after the start of the (b) process, further saccharify by using liquefying enzyme at the rate of 1 through 20 units per 1 g of substrate solid 1 through 48 hours after the beginning of the (b) process within a range such that maltose purity is 75 through 90% by weight and the value which is calculated with the following formula is not more than 7:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

wherein said maltogenic-α-amylase is produced by inserting the portion of the gene of *Bacillus stearothermophilus* coding for maltogenic-α-amylase into a plasmid and incorporating into *Bacillus subtilis*.

14. The method to manufacture high purity maltitol as described in claim 5, wherein the (c) process is a process to saccharify by using liquefying enzyme at the rate of 1 through 20 units per 1 g of substrate solid 1 through 10 hours after the start of the (b) process, further saccharify by using maltogenic-α-amylase at the rate of 1 through 20 units per 1 g of substrate solid within a range such that maltose purity is 75 through 88% by weight and the value which is calculated with the following formula is not more than 8:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

wherein said maltogenic-α-amylase is produced by inserting the portion of the gene of *Bacillus stearothermophilus* coding for maltogenic-α-amylase into a plasmid and incorporating into *Bacillus subtilis*.

15. The method to manufacture high purity maltitol as described in claim 2, wherein the (c) process is a process to continue saccharification, for 10 through 48 hours from the beginning of the (b) process, by using maltogenic-α-amylase which is produced by inserting the portion of the gene of *Bacillus stearothermophilus* coding for maltogenic-α-amylase into a plasmid and incorporating into *Bacillus subtilis*, 1 through 24 hours after starting the (b) process.

16. The method to manufacture high purity maltitol as described in claim 2, wherein the (c) process is a process to obtain saccharic liquid containing 94.5% by weight or more of maltose per solid substance in the liquid, by continuing saccharification, for 10 through 48 hours after the start of the (b) process, for the saccharic liquid from the (b) process 1 through 24 hours after the start of the (b) process obtained after adjusting pH of the liquid to not more than 4.5 and removing the residue, by using maltogenic-α-amylase which is produced by inserting the portion of the gene of *Bacillus stearothermophilus* coding for maltogenic-α-amylase into a plasmid and incorporating into *Bacillus subtilis*; thereafter, by hydrolyzing the dextrin in the liquid by using liquefying enzyme, filtrating and purifying the hydrolsate derived thereof.

17. The method to manufacture high purity maltitol as described in claim 6, wherein the (c) process is a process to saccharify by using liquefying enzyme at the rate of 1 through 20 units per 1 g of substrate solid 1 through 10 hours after the start of the (b) process, further saccharify by using maltogenic-α-amylase at the rate of 1 through 20 units per 1 g of substrate solid within a range such that maltose purity is 75 through 88% by weight and the value which is calculated with the following formula is not more than 8:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

wherein said maltogenic-α-amylase is produced by inserting the portion of the gene of *Bacillus stearothermophilus* coding for maltogenic-α-amylase into a plasmid and incorporating into *Bacillus subtilis*.

18. The method according to claim 1, wherein said process of liquefying starch utilizes a liquefying enzyme.

19. The method according to claim 1, wherein said maltogenic-α-amylase is produced by inserting the portion of the gene of *Bacillus stearothermophilus* coding for maltogenic-α-amylase into a plasmid and incorporating into *Bacillus subtilis*.

20. The method according to claim 1, consisting essentially of using the following four processes:
   (a) process of liquefying starch starch to produce a liquefied substance,
   (b) process of saccharifying the obtained liquefied substance by using at least two enzymes selected from the group consisting of β-amylase, pullulanase and isoamylase,
   (c) process of further saccharifying the obtained liquefied substance, after the start of the (b) process, by using glucoamylase or maltogenic-α-amylase, and
   (d) process for reducing saccharic liquid after completion of the (c) process utilizing a nickel or noble metal catalyst.

21. The method according to claim 5, wherein said maltogenic-α-amylase is produced by inserting the portion of the gene of *Bacillus stearothermophilus* coding for maltogenic-α-amylase into a plasmid and incorporating into *Bacillus subtilis*.

22. The method according to claim 5 consisting essentially of using the following four processes:
   (a) process of liquefying starch to a ground starch aqueous solution with a concentration of 5 through 40% by weight by using liquefying enzyme, and deactivating the liquefying enzyme at not more than DE 15,
   (b) process of saccharifying the liquefied substance obtained by the above process by using at least two enzymes selected from the group consisting of β-amylase, pullulanase and isoamylase,
   (c) process of further saccharifying the obtained liquefied substance by using glucoamylase or maltogenic-α-amylase after the start of the (b) process, having maltose purity of 75 through 90% by weight and limiting the value to not more than 8 when calculating it with the following formula:

$$\frac{\text{Weight of Solid Part of Oligosaccharides Being Trisaccharide or more}}{\text{Weight of Solid Part of Disaccharide + Weight of Solid Part of Oligosaccharides Being Trisaccharide or more}} \times 100$$

and
   (d) process of reducing the obtained saccharified substance by utilizing a nickel or noble metal catalyst.

* * * * *